US012653676B2

(12) United States Patent
Juhas et al.

(10) Patent No.: US 12,653,676 B2
(45) Date of Patent: Jun. 16, 2026

(54) PERSONALIZED MEDICAL DEVICE AND METHOD OF ITS PREPARATION

(71) Applicants: Juhamed S.R.O., Kosice-Myslava (SK); Technicka Univerzita V Kosiciach, Kosice-Sever (SK)

(72) Inventors: Martin Juhas, Baska (SK); Josef Zivcak, Presov (SK); Radovan Hudak, Kosice-Zapad (SK); Marek Schnitzer, Rozhanovce (SK); Branko Stefanovic, Kosice-Sidlisko Tahanovce (SK)

(73) Assignees: TECHNICKA UNIVERZITA V KOSICIACH, Kosice-Sever (SK); JUHAMED S.R.O., Kosice-Myslava (SK)

( * ) Notice: Subject to any disclaimer, the term of this patent is extended or adjusted under 35 U.S.C. 154(b) by 862 days.

(21) Appl. No.: 17/793,563

(22) PCT Filed: Feb. 12, 2021

(86) PCT No.: PCT/SK2021/050002
§ 371 (c)(1),
(2) Date: Jul. 18, 2022

(87) PCT Pub. No.: WO2021/167539
PCT Pub. Date: Aug. 26, 2021

(65) Prior Publication Data
US 2023/0130215 A1 Apr. 27, 2023

(30) Foreign Application Priority Data

Feb. 17, 2020 (SK) .................................. PP 8-2020
Feb. 17, 2020 (SK) ......................... PUV 17-2020 U

(51) Int. Cl.
*A61F 2/28* (2006.01)
*A61L 27/16* (2006.01)
(Continued)

(52) U.S. Cl.
CPC ............ *A61F 2/2803* (2013.01); *A61L 27/16* (2013.01); *A61L 27/18* (2013.01); *A61L 27/446* (2013.01);
(Continued)

(58) Field of Classification Search
CPC .......... A61F 2/2803; A61F 2002/30985; A61F 2002/30952; B33Y 50/00; B33Y 40/20;
(Continued)

(56) References Cited

U.S. PATENT DOCUMENTS

| | | | |
|---|---|---|---|
| 11,712,208 B2 * | 8/2023 | Nye ..................... | A61B 5/0013 |
| | | | 382/128 |
| 2010/0217338 A1 * | 8/2010 | Carroll .................. | A61B 34/10 |
| | | | 606/86 R |

(Continued)

FOREIGN PATENT DOCUMENTS

CN 107981944 A 5/2018

OTHER PUBLICATIONS

International Search Report and Written Opinion dated Jun. 8, 2021 for related PCT Patent Application No. PCT/SK2021/050002 which was filed on Feb. 12, 2021; 14 pages.

(Continued)

*Primary Examiner* — Allen H Nguyen
(74) *Attorney, Agent, or Firm* — Hovey Williams LLP; Paul J. Walker

(57) ABSTRACT
A personalized medical device intended for correction of defects, in particular in the orofacial area is multicomposite and comprises a hard tissue replacement and a soft tissue replacement. The hard tissue replacement is a hard core of biocompatible thermoplastic material and the soft tissue replacement is a biocompatible elastic substance. Preparation of personalized medical device even in the prenatal (Continued)

period using CT, MRI and 3D/4D electronic USG imaging and "additive manufacturing" technology.

4 Claims, 1 Drawing Sheet

(51) Int. Cl.

| | |
|---|---|
| *A61L 27/18* | (2006.01) |
| *A61L 27/44* | (2006.01) |
| *A61L 27/50* | (2006.01) |
| *B33Y 40/20* | (2020.01) |
| *B33Y 50/00* | (2015.01) |
| *B33Y 80/00* | (2015.01) |
| *A61F 2/30* | (2006.01) |

(52) U.S. Cl.
CPC .............. *A61L 27/50* (2013.01); *B33Y 40/20* (2020.01); *B33Y 50/00* (2014.12); *B33Y 80/00* (2014.12); *A61F 2002/30952* (2013.01); *A61F 2002/30985* (2013.01); *A61L 2430/02* (2013.01); *A61L 2430/34* (2013.01)

(58) Field of Classification Search
CPC .......... B33Y 80/00; A61L 27/16; A61L 27/18; A61L 27/446; A61L 27/50; A61L 2430/02; A61L 2430/34

USPC ........................................................ 382/128
See application file for complete search history.

(56) References Cited

U.S. PATENT DOCUMENTS

| | | | |
|---|---|---|---|
| 2013/0084636 A1 | 4/2013 | Cho | |
| 2015/0262387 A1* | 9/2015 | Zebaze .................. | A61B 6/505 |
| | | | 382/128 |
| 2016/0206786 A1 | 7/2016 | Ellman et al. | |
| 2021/0339047 A1* | 11/2021 | Janardhanan ........ | A61N 5/1031 |
| 2022/0126117 A1* | 4/2022 | Voronenko .......... | A61N 5/1084 |

OTHER PUBLICATIONS

Riedle, Hannah et al.; "Generation of 3D Silicone Models of Anatomic Soft Tissue Structures—A Comparison of Direct 3D Printing and Molding Techniques"; 2018 IEEE-EMBS Conference on Biomedical Engineering and Sciences (IECBES); Dec. 3, 2018; pp. 539-543.

Martin Del Campo, Marcela et al.: "Biomaterials for Cleft Lip and Palate Regeneration"; International Journal of Molecular Sciences, vol. 20, No. 9, May 2, 2019; p. 2176.

Mills, David et al.; "The Use of 3D Printing in the Fabrication of Nasal Stents"; Inventions, vol. 3, No. 1, Dec. 23, 2017; p. 2.

* cited by examiner

PERSONALIZED MEDICAL DEVICE AND METHOD OF ITS PREPARATION

RELATED APPLICATIONS

This application is the National Stage of International Patent Application No. PCT/SK2021/050002, filed Feb. 12, 2021, which is hereby incorporated herein by reference in its entirety, and which claims priority to Slovakian Patent Application No. PP 8-2020, filed Feb. 17, 2020, and Slovakian Patent Application No. PUV 17-2020, filed Feb. 17, 2020, which are also incorporated herein by reference in their entirety.

TECHNICAL FIELD

The invention relates to a personalized medical device intended for correction of defects, in particular in the orofacial area, and to a method of its preparation, and belongs to the field of healthcare.

BACKGROUND ART

The biological functionality of an adequately prenatally developed hard and soft palate ensures the normal development of the respiratory and suction reflex as well as the related normal alimony ability and auditory conformity immediately postnatally in a human individual. In the late period of infancy, or in the period of the toddler, in the case of a palate unaffected by cleft, the normal development of speech, phonetics with the correct development of auditory perception of speech is ensured. In the period of preschool and school age, this ensures the normal psychomotor and psychosocial development of such a child. Said important functions can be significantly limited postnatally to varying degrees in the embryonic or prenatal phase of abnormal development of hard or soft palate, when they are affected by different types of cleft of hard or soft palate.

In the case of congenital clefts of orophation with an intervention in the area of the maxillary alveolar arch and in the hard palate area is nowadays applied postnatally in pre-surgical correction (PSO) (based on the impression-imprint technique modified according to Figuero and Grayson) produced by the so-called active temporary modulation device based on WHO recommendations: *Global strategies to reduce the health-care burden of craniofacial anomalies of year* 2002 and *AAPD and ACPA: Policy on the Management of Patients with Cleft Lip/Palate and Other Craniofacial Anomalies of year* 2012. According to available studies, pre-surgical correction (PSO) and so-called presurgical nasoalveolar molding (PNAM) undoubtedly has several advantages, such as:

retrospective correction of protruding premaxilla,
  non-surgical reduction of the size of the alveolar gap,
  non-surgical extension of the columella,
  approximately 60% of patients treated in this way do not require surgical secondary bone transplantation,
  early restart of maxillary alveolar arch growth,
  improvement of the final symmetry of the nose after correction,
  promoting intra-oral food intake,
  Current pre-surgical correction (PSO) and the so-called presurgical nasoalveolar molding (PNAM) also has several negative effects:
  irritation to ulceration of oral, gingival and nasal mucosa and buccal skin,
  moving or removing the device by child's tongue, fungal infections of the oral mucosa,
  formation of a mega-nostril due to excessive pressure on the nasal cartilage,
  formation of an asymmetric T-shape configuration of two parts of the maxillary alveolar arch separated by a cleft,
  approximately 30% of devices break through wear,
  Similarly, other congenital malformations can thus damage a person's further biological, psychological and social development in the early as well as later child's postnatal phase of a person's life. As we can currently identify almost 98% of structural congenital developmental abnormalities using imaging methods (USG, MRI, CT), we now need to establish a system for the prenatal process and a method for creating individualized custom-made medical devices, replacements and implants made by the "additive manufacturing" system. Personalized inserts from additive manufacturing fully correlate and take into account the anatomy of the selected individual and solve problems associated with the responses of the patient's body to non-personalized products and components and the late time frame of their application due to the length of postnatal error description and postnatal production.

In the long run, i.e. over a period of 20 years, in the field of temporary neonatal palate replacements, form of imprint production of a single-composite palate temporary replacement based on vinylpolysiloxanes or light polymerizing acrylates is mainly used. However, these types of replacements bring with them unavoidable limits in terms of the replacement of the hard palate absent due to cleft, namely in the effectiveness of sealing faulty communications with the nasal cavity, the absent part of the soft palate replacement during alimentation and last but not least vector mechanics in the area of displacement of interest in the process of maxillary orthopaedic-anatomical correction. The impact of the ineffectiveness of these temporary replacements on the affected individual in the first days to weeks of the neonatal age stage brings fatal consequences to his further plastic-corrective management, speech therapy articulation development, psychological affectation, educational process and social-work classification. Also, the attachment of these replacements brings significant discomfort for the facial part of the individual and the associated ineffective cooperation between doctor-patient and doctor-parent.

The current state in the field of pre-surgical correction of cleft maxillary alveolar arch defects, premaxil and palate is the choice of production of single-composite impression implants in the time horizon of about 1 to 12 weeks from the birth of a newborn. Pre-surgical correction is based on the classification description Kernahan's striped Y logo (year 1971): Block 1 and 4: lip, Block 2 and 5: alveolar arch, Block 3 and 6: anterior hard palate after incisive foramen, Block 7 and 8: posterior hard palate after posterior nasal spine, Block 9: soft palate, or from a modified Kernahan's classification developed by the American Cleft Association (Harkins et al., 1982): Prepalatal clefts (lip, alveolar arch, unilateral, central, bilateral), Palatal clefts (hard and soft palate), Prepalatal and palatal clefts (combinations).

Based on these classifications, a specific, although limited, algorithm is developed in the further postnatal management of such an affected individual. Until now, routine practice has applied time procedures in the care of individuals affected by cleft orophation based only on a postnatal algorithm developed in the second half of the twentieth century by specialists from the Children's Hospital of Philadelphia (year 1971).

The analysis of the current state in the field of production of temporary medical surgical devices for cleft management of orophation is based only on the postnatal period, as the whole algorithm of clinical steps currently applies only to this period. The current postnatal production of orofacial temporary cleft replacements is based on two aspects of presurgical nasoalveolar molding (PNAM) production.

A.) Postnatal Traditional Workflow:

By means of mechanical impression of PVS mass against topoanatomical structures of interest in cleft-affected maxillary and palatal part of orophation, Creation of a negative plastic model after solidification of PVS mass, Laboratory manual design and final production based on the empirical anatomical imagination of the relevant laboratory technician.

B.) Postnatal Digital Workflow:

Digital scan of hard palate postnatal plaster imprint,

Software design of digital plaster imprint scan, 3D printing of the replacement, Application of replacement.

The above production of postnatal pre-surgical orofacial devices is also based on the following patent solutions RU2369347C1, US 2011/0060438 A1, RU94450U1, US 2015/0164676 A1, U.S. Pat. No. 8,323,308B2, CN101673481A, RU2593235C1 and scientific articles:

Bauer, F., Schönberger, M., Gattinger, J., et al. (2017). *RapidNAM: generative manufacturing approach of nasoalveolar molding devices for presurgical cleft lip and palate treatment. Biomedical Engineering/Biomedizinische Technik,* 62 (4), pp. 407-414. Retrieved 18 May 2018, from doi:10.1515/bmt-2016-0035;

Loeffelbein D. J., Rau A., Wolff K.-D.: *Impression technique for monitoring and virtual treatment planning in nasoalveolar moulding: British Journal of Oral and Maxillofacial Surgery* (2013), 51 (8), pp. 898-901;

Quan, Y, Gong, X., Guo-Min, W. et al.: *A Novel Technique for Presurgical Nasoalveolar Molding Using Computer-Aided Reverse Engineering and Rapid Prototyping: Journal of Craniofacial Surgery January* (2011), 22 (1), pp. 142-146;

Ritschl, L. M., et al.: *Pitfalls and solutions in virtual design of nasoalveolar molding plates by using CAD/CAM technology—A preliminary clinical study: J Craniomaxillofac Surg.* (2016), 44 (4), pp. 453-459.

BRIEF DESCRIPTION OF THE DRAWINGS

FIG. 1 illustrates a personalized medical device (1) intended for correction of defects in the orofacial area, designed as a multicomposite structure comprising a hard tissue replacement (2) and a soft tissue replacement (3). The hard tissue replacement (2) forms a bone tissue replacement and constitutes the mechanically load-bearing part of the device. It is manufactured form a biocompatible thermoplastic material, wherein: for a non-implantable device, the material is polyphenylsulfone/polypropylene sulfone (PPSU), and for an implantable device, the material is a synthetic, osseointegratable, non-resorbable material selected from polyaryl ketones (PAEK), polyaryl ketones in combination with ceramics, or polyaryl ketones in combination with ceramics and reinforcement. The soft tissue replacement (3) is arranged on and partially envelops the hard tissue replacement (2) and is formed from a biocompatible elastic substance intended to replace muscle and epithelial soft tissue.

FIG. 2 emphasizes the functional integration between the hard tissue replacement (2) and the soft tissue replacement (3). The hard tissue replacement (2) is clearly visible as as bone-substituting core, providing structural stability and shape fidelity. The soft tissue replacement (3) surrounds and interfaces with the hard component, forming a biologically compatible elastic layer that simulates muscle and epithelial tissues. A material and geometric interface region (4) is formed between the hard tissue replacement (2) and the soft tissue replacement (3), allowing gradual transfer of mechanical loads, reduction of stress concentrations, and improved biological, functional, and aesthetic integration of the device in the orofacial area. FIG. 2 highlights the patient-specific geometry of the device (1) and the multi-material composition enabling its use as either an implantable or non-implantable personalized medical solution.

NATURE OF INVENTION

Figure 1:
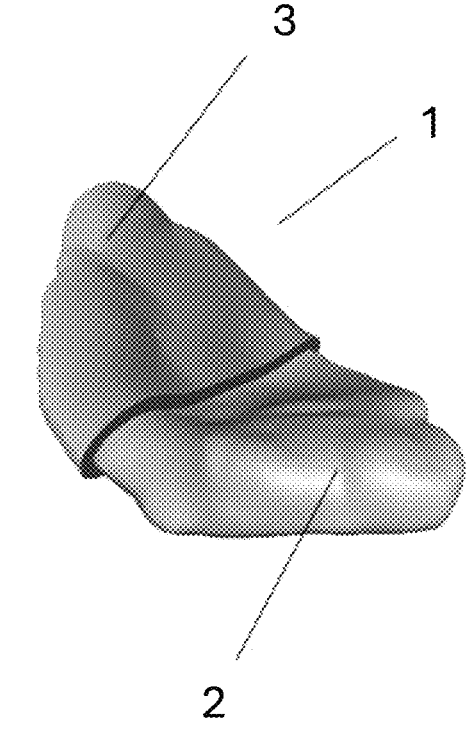
FIG. 1 is a partial cutaway perspective view of a personalized medical device including a multicomposite layered structure in accordance with an embodiment of the invention.
Figure 2:
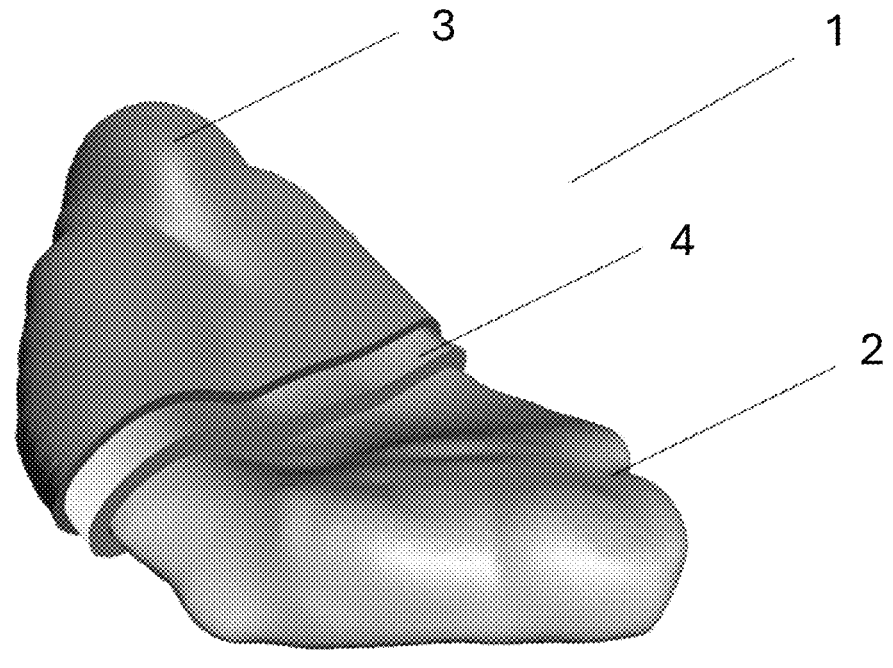
FIG. 2 is another partial cutaway perspective view of the personalized multicomposite medical device of FIG. 1.

The personalized medical device and the method of its preparation according to present invention, in particular the orofacial personalized medical device in the PNAM process bring a significant advance in the creation and production of medical devices, in particular for clefts of the face and palate by a system of their individualization for individuals with the intervention of creating a replacement of hard and soft palate even in prenatal period using CT, MRI and 3D/4D electronic USG imaging and 3D printing additive production technology.

The personalized medical device intended for correction of defects, in particular in the orofacial area, is multicomposite and comprises a hard tissue replacement and a soft tissue replacement. The hard tissue replacement is a hard core of biocompatible thermoplastic material and the soft tissue replacement is a biocompatible elastic substance. The medical device may be implantable as well as non-implantable.

The biocompatible thermoplastic material for the non-implantable device may be from the group of hardened silicone, methacrylate-based substances, polypropylene sulfone.

The biocompatible thermoplastic material for the implantable device may be a synthetic osseointegratable bioresorbable material or a synthetic osseointegratable non-resorbable material.

The synthetic osseointegratable bioresorbable material may be polycaprolactone and the synthetic osseointegratable non-resorbable material may be polyaryl ketones or polyaryl ketones in combination with ceramics or polyaryl ketones in combination with ceramics and with reinforcement. The reinforcement can be made of carbon and/or glass fibres.

The biocompatible elastic substance for the non-implantable device may be based on elastic silicone or polyurethane and for the implantable device may be an epithelial colony of a corrected defect.

It is advantageous if the surface treatment of the hard core of biocompatible thermoplastic material is adapted to attach even the soft tissue of the cleft. The surface treatment of the hard core can be solved by coating or dipping.

It is advantageous if the shape of the personalized medical device is adapted to attach to an alveolar arch.

The process of production a personalized medical device according to this invention is unique, as evidenced by the complete worldwide literature absence for the creation of such replacements by said innovative and modern process. In any case, attempts at centralized production of medical devices in form of 3D printing of medical devices from 3D/4D fetal sonography have already been reported for 2016 in scientific peer-reviewed journals for ultrasound gyneco-logical and obstetric specialists. However, these articles provide only a look at 3D prints as academic tools for modelling the fidelity of structures, such as placental pathologies, facial dysmorphia, limb abnormalities, fetal heart anatomy, and their plastic models for graduate educa-tion. However, so far with virtually no benefit for the direct clinical therapeutic solution of the patient.

The process of clinical defect management based on prenatal additive manufacturing of the individualized PNAM device changes the postnatal management so far in the first three phases to the prenatal-fetal period.

The nature and uniqueness of the invention is based on prenatal production in form of additive manufacturing of the multicomposite pre-surgical device PNAM personalized to measure with the possibility for its immediate postnatal applicability to the newborn. Prenatal production and indi-vidualization of such devices for an individual depends on the quality of DICOM data collection from a properly timed prenatal implementation of 3D/4D mechanical and digital USG visualization of cleft of fetal orophation. 3D USG visualization and its optimization consists of several steps:

a) Preparation of image dataset of 2D image sections of interest of damaged hard and soft tissues of fetal orophation obtained by USG visualization.

b) The prepared image dataset of 2D image sections of interest undergoes by multiplanar, rendering, sectional and volume adjustment of individual 2D image sec-tions of interest to a 3D ultrasound dataset of anthro-pometric and anatomical data. The whole process requires detailed and accurate editing of three perpen-dicular planes to each other for the most detailed depiction of orofacial cleft pathologies.

c) Subsequently taken 3D ultrasound dataset of the scanned sections is processed into the output 3D image format.

d) The most suitable anatomical areas of interest are selected by post-processing processing.

e) Subsequently the modelling of the PNAM device itself is realized, which includes both hard and soft palate.

f) Subsequently the 3D image format is compared also with MRI and CT imaging of fetal orophation.

g) A 3D/4D ultrasound, CT and MRI algorithm for displaying facial clefts with the creation of post-pro-cessing output of DICOM data for 3D modelling and processing for additive manufacturing in form of 3D printing is created.

h) Anthropometric and anatomical data using DICOM editable software platforms are evaluated and a digital reference model in form of a STL network model with accurate localization of the hard and soft tissues defect is created.

i) The extent of hard and soft tissue deformation is measured exactly on a digital reference model;

j) Based on a digital reference model, a digital personal-ized medical device is created;

k) a clinically applicable model of a personalized multi-composite medical device containing hard tissue and soft tissue replacement is produced;

l) followed by prenatal production of a multicomposite device for PNAM to measure also with supplementa-tion of the cleft-affected soft palate.

It is advantageous to surface-treat the hard tissue replace-ment. This can be done by coating or dipping.

Prior to producing a clinically applicable model of the personalized medical device, is appropriate to additively produce a reference model of the deformity itself as well as a medical device model, wherein there are validated dimen-sions on the reference models and are considered by con-sultation in terms of fixation and application parameters.

The disadvantages of the present solutions are overcome by the features of the present invention. The advantages achieved by the multicomposite personalized medical device intended for correction of defects, in particular in the orofacial area according to this invention, are as follows:

temporality (immediately applicable after delivery), significant reduction of facial discomfort (grip of the device is typed only on the alveolar arch and not on the extraoral areas of the face), improved alimentation (more precise anatomical bridging of cleft surfaces and implemented replacement of soft palate into multicomposite replacement), more targeted mechanical action from the point of view of maxillary orthopaedic correction and a more optimized approach for the final solution with plastic surgical correction.

This invention has been prepared with the support of the following grants: APVV-17-0278, APVV-15-0111, APVV-15-0356, VEGA 1/0179/19, Incentives for Research and Development, no. of agreement 1223/2018.

EXAMPLES OF EMBODIMENTS

Example 1

A personalized medical device according to this invention intended for correction of defects in the orofacial area is prepared. It is multicomposite and comprises a hard tissue replacement and a soft tissue replacement. The hard tissue replacement is a hard core of biocompatible thermoplastic material and the soft tissue replacement is a biocompatible elastic substance. The medical device is non-implantable.

A biocompatible thermoplastic material used as a hard tissue replacement in this example of embodiment is hard-ened silicone.

A biocompatible elastic material used as a soft tissue replacement in this example of embodiment is elastic sili-cone.

The surface treatment of the hard core of hardened silicone is adapted to attach even the cleft-affected soft tissue. In this example of embodiment, the surface treatment is solved by coating.

The shape of the personalized medical device is adapted to attach to an alveolar arch.

A method for preparation of the personalized medical device according to this example of embodiment comprises the following steps:

preparation of image dataset of 2D image sections of interest of damaged hard and soft tissues of fetal orophation obtained by USG visualization;

| USG image plane | Visualization benefits | Visualization restrictions |
|---|---|---|
| Transverse-ventral | Clear diagnosis of cleft extent and depth | Feasible only if the fetus is in an adequate position |

7

-continued

| USG image plane | Visualization benefits | Visualization restrictions |
| --- | --- | --- |
| Transverse-lateral | An section suitable for examination for the extent of a lip defect, but limited to some extent in the description of a bone defect | In the case of bilateral clefts, exposure to a possible inadequate definition of the defect, which may be located even more distal from the probe |
| Oblique-lips | Excellent plane for examination of lip defect and possible abnormalities of alae nasi | Feasible only if the fetus is in an adequate position |
| Oblique-palate | Good approach for the examination of cleft bone defects and their relationship to the nasal cavity | Feasible only if the fetus is in an adequate position. It also does not give information about the lips. |
| Coronal-facial | Good area for imaging central defects of the nose and lip | A lateral defect does not appear in this type of section |
| Midsagittal-profile | It allows to detect and distinguish the adjacent area of the soft tissue of the palate, uvula and philtrum in bilateral clefts | No information about unilateral clefts except philtrum cleft | the prepared image dataset of 2D image sections of interest of three mutually perpendicular planes is adjusted by multiplanar, rendering, sectional and volume adjustment to a 3D ultrasound dataset of anthropometric and anatomical data;

the prepared 3D ultrasound dataset of the scanned sections is processed into the output 3D image format;

the most suitable anatomical areas of interest are selected by post-processing processing of 3D image format;

subsequently the modelling of the PNAM device itself is realized, which includes both hard and soft palate.

subsequently the 3D image format is compared also with MRI and CT imaging of fetal orophation;

a 3D/4D ultrasound, CT and MRI algorithm for displaying facial clefts with the creation of post-processing output of DICOM data for 3D modelling and processing for additive manufacturing in form of 3D printing is created.

anthropometric and anatomical data using DICOM editable software platforms are evaluated and a digital reference model in form of a STL network model with accurate localization of the hard and soft tissues defect is created;

the extent of hard and soft tissue deformation is measured exactly on a digital reference model;

based on a digital reference model, a digital personalized medical device is created;

a clinically applicable model of a personalized multicomposite medical device is produced.

The preparation of a personalized medical device takes place in the prenatal period and postnatal period. The prenatally prepared device can be immediately administered postnatally to the newborn.

Prior to producing a clinically applicable model of the personalized medical device, a reference model of the deformity itself as well as a medical device model is additively produced, wherein there are validated dimensions on the reference models and are considered by consultation in terms of fixation and application parameters.

Example 2

The personalized medical device and method of its preparation according to this example of embodiment are identical to Example 1, except that a biocompatible thermoplastic material used as a hard tissue replacement in this example of embodiment is polymethyl methacrylate and a biocompatible elastic substance used as a soft tissue replacement in this example of embodiment is elastic silicone.

In this example of embodiment, the surface treatment of the hard tissue is solved by dipping.

Example 3

The personalized medical device and method of its preparation according to this example of embodiment are identical to Example 1, except that a biocompatible thermoplastic material used as a hard tissue replacement in this example of embodiment is polymethyl methacrylate and a biocompatible elastic substance used as a soft tissue replacement in this example of embodiment is polyurethane.

Example 4

The personalized medical device and method of its preparation according to this example of embodiment are identical to Example 1, except that a biocompatible thermoplastic material used as a hard tissue replacement in this example of embodiment is polypropylene sulfone and a biocompatible elastic substance used as a soft tissue replacement in this example of embodiment is elastic silicone.

Example 5

The personalized medical device and method of its preparation according to this example of embodiment are identical to Example 1, except that a biocompatible thermoplastic material used as a hard tissue replacement in this example of embodiment is polypropylene sulfone and a biocompatible elastic substance used as a soft tissue replacement in this example of embodiment is polyurethane.

Example 6

The personalized medical device and method of its preparation according to this example of embodiment are identical to Example 1, except that it is an implantable medical device and a biocompatible thermoplastic material used as a hard tissue replacement in this example of embodiment is bioresorbable, osseointegratable polycaprolactone and a biocompatible elastic substance used as a soft tissue replacement in this example of embodiment is epithelial colony replacing the mucosa of the soft palate.

Example 7

The personalized medical device and method of its preparation according to this example of embodiment are identical to Example 1, except that it is an implantable medical device and a biocompatible thermoplastic material used as a hard tissue replacement in this example of embodiment are non-resorbable, osseointegratable polyaryl ketones and a biocompatible elastic substance used as a soft tissue replacement in this example of embodiment is epithelial colony replacing the mucosa of the soft palate.

Example 8

The personalized medical device and method of its preparation according to this example of embodiment are identical to Example 1, except that it is an implantable medical device and a biocompatible thermoplastic material used as a hard tissue replacement in this example of embodiment are non-resorbable, osseointegratable polyaryl ketones in combination with ceramics and a biocompatible elastic substance used as a soft tissue replacement in this example of embodiment is epithelial colony replacing the mucosa of the soft palate.

INDUSTRIAL APPLICABILITY

The industrial applicability of the invention is obvious. The personalized medical device according to this invention is intended in particular for correction of defects in the orofacial area and for its preparation in the prenatal period as well as in the postnatal period. However, the use of the invention is also possible for the production of personalized medical devices as a replacement for other parts of the human body.

The invention claimed is:

1. A method for preparation of a personalized medical device intended for correction of defects in the orofacial area, which is multi-composite and comprises a hard tissue replacement and a soft tissue replacement, wherein the hard tissue replacement is a bone tissue replacement of biocompatible thermoplastic material and the soft tissue replacement is a muscle and epithelial soft tissue replacement of biocompatible elastic substance, wherein the biocompatible thermoplastic material for the non-implantable device is polypropylene sulfone and the biocompatible thermoplastic material for the implantable device is a synthetic osseointegratable non-resorbable material which are polyaryl ketones or polyaryl ketones in combination with ceramics or polyaryl ketones in combination with ceramics and with reinforcement, wherein the method takes place at the prenatal time examined by CT, MRI, USG to obtain DICOM data and comprises the following steps:

a) preparation of image dataset of 2D image sections of interest of damaged hard and soft tissues of fetal orophation obtained by USG visualization;

b) the prepared image dataset of 2D image sections of interest of three mutually perpendicular planes is adjusted by multiplanar, rendering, sectional and volume adjustment to a 3D ultrasound dataset of anthropometric and anatomical data;

c) the prepared 3D ultrasound dataset of the scanned sections is processed into the output 3D image format;

d) the most suitable anatomical areas of interest are selected by post-processing processing of 3D image format;

e) subsequently the modelling of the PNAM device itself is realized, which includes both hard and soft palate;

f) subsequently the 3D image format is compared also with MRI and CT imaging of fetal orophation;

g) a 3D/4D ultrasound, CT and MRI algorithm for displaying facial clefts with the creation of post-processing output of DICOM data for 3D modelling and processing for additive manufacturing in form of 3D printing is created-;

h) anthropometric and anatomical data using DICOM editable software platforms are evaluated and a digital reference model in form of a STL network model with accurate localization of the hard and soft tissues defect is created;

i) the extent of hard and soft tissue deformation is measured exactly on a digital reference model;

j) based on a digital reference model, a digital personalized medical device is created;

k) a clinically applicable model of a personalized multi-composite medical device containing hard tissue and soft tissue replacement is produced.

2. The method for preparation of the personalized medical device according to claim 1, wherein the hard tissue replacement is surface treated by coating or dipping.

3. The method for preparation of the personalized medical device according to claim 2, wherein the surface treatment of the hard tissue replacement is adapted to attach residual cleft-affected soft tissue of orophation.

4. The method for preparation of the personalized medical device according to claim 1, wherein prior to producing a clinically applicable model of the personalized medical device, a reference model of the deformity itself as well as a medical device model is additively produced, wherein there are validated dimensions on the reference models and are considered by consultation in terms of fixation and application parameters.

\* \* \* \* \*